(12) United States Patent
Hessefort et al.

(10) Patent No.: US 8,829,118 B2
(45) Date of Patent: Sep. 9, 2014

(54) METHOD FOR USING HYDROPHOBICALLY MODIFIED POLYMERS IN CONSUMER AND INDUSTRIAL APPLICATIONS

(75) Inventors: Yin Z. Hessefort, Naperville, IL (US); Patrick J. Marek, Chicago, IL (US); Jeffrey R. Cramm, Batavia, IL (US); Damyanti J. Patel, Hoffman Estates, IL (US); Wayne M. Carlson, Batavia, IL (US)

(73) Assignee: Nalco Company, Naperville, IL (US)

( * ) Notice: Subject to any disclaimer, the term of this patent is extended or adjusted under 35 U.S.C. 154(b) by 309 days.

(21) Appl. No.: 12/575,966

(22) Filed: Oct. 8, 2009

(65) Prior Publication Data

US 2010/0093582 A1  Apr. 15, 2010

Related U.S. Application Data

(63) Continuation-in-part of application No. 11/853,084, filed on Sep. 11, 2007, now abandoned.

(51) Int. Cl.
*C11D 3/37* (2006.01)
*A61K 8/81* (2006.01)
*A61Q 5/02* (2006.01)
*C08L 33/26* (2006.01)
*C08F 8/32* (2006.01)

(52) U.S. Cl.
CPC ... *C08F 8/32* (2013.01); *A61Q 5/02* (2013.01); *C08L 33/26* (2013.01); *A61K 8/8158* (2013.01); *C11D 3/3769* (2013.01); *C11D 3/378* (2013.01)
USPC ........ 525/329.7; 510/109; 510/119; 510/130; 510/475

(58) Field of Classification Search
USPC ......... 526/317.1, 318, 303.1; 427/384, 389.9; 525/329.7; 510/109, 119, 130, 278, 510/475
See application file for complete search history.

(56) References Cited

U.S. PATENT DOCUMENTS

| 2,438,091 A | 3/1948 | Lynch |
| 2,528,378 A | 10/1950 | Mannheimer |
| 2,658,072 A | 11/1953 | Kosmin |
| 4,694,046 A | 9/1987 | Bock et al. |
| 4,921,903 A | 5/1990 | Fong |
| 5,196,052 A | 3/1993 | Gross et al. |
| 5,573,709 A | 11/1996 | Wells |
| 6,303,190 B1 * | 10/2001 | Linert et al. .................. 427/387 |
| 2005/0129653 A1 * | 6/2005 | Hessefort et al. .......... 424/70.16 |

FOREIGN PATENT DOCUMENTS

| EP | 0231997 | 8/1987 |
| GB | 2260985 A | 5/1993 |
| JP | 2004067650 A | 3/2004 |
| WO | WO0049999 A | 8/2000 |
| WO | WO0071651 A2 | 11/2000 |
| WO | WO02083085 A1 | 10/2002 |
| WO | WO2006/081496 A2 | 8/2006 |

OTHER PUBLICATIONS

Angelinetta, C. et al., "Hydrophobic hydroxypropyl guar: A natural polymer modified for cosmetic use," Cosmetic News, 1995, vol. 18, No. 104, pp. 338-341.
Drovetskaya, T.V. et al., "Effects of low-level hydrophobic substitution on conditioning properties of cationic cellulosic polymers in shampoo Systems," Journal of Cosmetic Science, 2004, vol. 55, (Supplement) pp. S195-S205.
Freese, R.G. et al., "A New Amphoteric Surfactant Series for Shampoo Use," American Perfumer and Aromatics, 1956, vol. 67, No. 3, pp. 37-40.

* cited by examiner

Primary Examiner — Ling Choi
Assistant Examiner — Chun-Cheng Wang
(74) Attorney, Agent, or Firm — Edward O. Yonter

(57) ABSTRACT

This invention pertains to method of using a composition comprising one or more hydrophobically modified polyacrylamides, wherein the polyacrylamides contain acrylamide, one or more anionic monomers, and excludes a cationic monomer, and the method of combination with other compositions for use in combination for consumer and/or industrial applications.

18 Claims, No Drawings

METHOD FOR USING HYDROPHOBICALLY MODIFIED POLYMERS IN CONSUMER AND INDUSTRIAL APPLICATIONS

CROSS-REFERENCE TO RELATED APPLICATIONS

This application is a continuation in part application claiming priority from application Ser. No. 11/853,084 which was filed on Sep. 11, 2007 now abandoned.

FIELD OF THE INVENTION

This invention pertains to a method of using hydrophobically modified polyacrylamide composition for consumer and/or industrial applications.

BACKGROUND OF THE INVENTION

Surfactants have been widely formulated in cleansing products in cosmetic applications. The major function of surfactants in rinse off products is to cleanse the skin and hair of fatty and water-soluble impurities, however, surfactants meanwhile also cause irritation.

In skin care applications, surfactants function to remove normal skin lipids. The natural water-lipid film that functions to protect the skin is disturbed with every wash. Hydrophilic groups of the negatively charged polar surfactant anions react with the weakly cationic, positively charged amino groups of proteins of the skin and mucosa. Therefore, surfactants are known for their irritancy to eyes and defatting to skin, this is especially the case for anionic surfactants, which react with proteins in the skin and mucous membranes. The similar defatting effect from surfactant is also true in hair care. The most critically assessed surfactants are sodium lauryl and laureth sulfate, which can significantly cause hair harshness after the shampooing.

Another important aspect of surfactants is their foaming properties. Consumer's perception of foam is physiologically related to the efficacy of cleansing. The products that generate large volume and size of foam during application are often perceived to have better a cleansing effect. The typical surfactants of fatty alcohol sulfates generate good amounts of foam with medium to large foam bubble sizes.

In both hair care and skin care applications, many polymeric conditioners and emollients are inherently hydrophobic and they tend to be difficult to be spread and can leave deposits left on skin or hair if the formulation has poor wetting properties. Therefore, wetting is another important property to be assessed. Surface tension is used as one of the tools for the evaluation of wetting property. Common surfactants, e.g. fatty alcohol sulfates, have low surface tension, which helps to enhance the wetting attribute in formulations for hair and skin.

One major concern for surfactants is their irritancy. Many studies have been done over the decades to reduce the irritancy and defatting disadvantages of surfactants. However, over the course of the development of low irritancy surfactants, scientists often have a dilemma: in exchange for low irritancy the foam property was sacrificed.

An alternative surfactant to fatty alcohol sulfates is therefore desired.

SUMMARY OF THE INVENTION

The present disclosure provides for a method of using a composition comprising one or more hydrophobically modified polyacrylamides, wherein the polyacrylamides contain acrylamide, one or more anionic monomers, and excludes a cationic monomer.

The present disclosure also provides for a method of treating a substrate comprising applying the composition to a substrate or a surface.

DETAILED DESCRIPTION OF THE INVENTION

Definitions

"Anionic monomer" means a monomer, which possesses a net negative charge. Representative anionic monomers include base addition salts of acrylic acid, methacrylic acid, itaconic acid, 2-acrylamido-2-methyl-1-propanesulfonic acid, sulfopropyl acrylate or methacrylate or other water-soluble forms of these or other polymerizable carboxylic or sulfonic acids, sulphomethylated acrylamide, allyl sulphonate, styrene sulfonic acid, sodium vinyl sulphonate, and the like. Preferred anionic monomers are acrylic acid and 2-acrylamido-2-methyl-1-propanesulfonic acid.

"Base addition salt" means the salt resulting from reaction of a carboxylic acid ($-CO_2H$) group with a suitable base such as the hydroxide, carbonate, or bicarbonate of a metal cation or tetraalkylammonium cation, or with ammonia, or an organic primary, secondary, or tertiary amine of sufficient basicity to form a salt with the carboxylic acid group. Representative alkali or alkaline earth metal salts include sodium, lithium, potassium, calcium, magnesium, and the like. Representative organic amines useful for the formation of base addition salts include ethylamine, diethylamine, ethylenediamine, ethanolamine, diethanolamine, piperazine, and the like. Preferred base addition salts include the sodium and ammonium salts.

"Hydrophobic alkyl group" means an alkyl, alkenyl, cycloalkyl, aryl or arylalkyl group of about 4 to about 22 carbon atoms. Alkyl and alkenyl groups may be straight or branched and may be interrupted with one or more —OSi(R')(R")— and —Si(R')(R")— groups wherein R' and R" are $C_1$-$C_4$ alkyl.

"Hydrophobic amine" means a compound containing at least one hydrophobic alkyl group and at least one amino hydrogen atom capable of undergoing a transamidation reaction with an amido ($-C(O)NH_2$) group of a polyacrylamide as defined herein to form a hydrophobically modified polyacrylamide. Hydrophobic amines containing —OSi(R')(R")— and —Si(R')(R")— groups are also referred to as "amino-functionalized silanes". Representative hydrophobic amines include benzylamine, cyclohexylamine, hexylamine, methylhexylamine, phenethylamine, octylamine, oleylamine, decylamine, dodecylamine, octadecylamine, and the like.

Representative amino-functionalized silanes include amines of formula

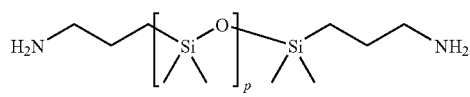

wherein p is about 5 to about 500, available from Aldrich, Milwaukee, Wis.; aminoethylpropyl silicone compounds available from Noveon, Cleveland, Ohio under the trade name Ultrasil and from Siltech Corporation, Toronto, Ontario, Canada under the trade name Silamine; and amine functional silicones including Dow Corning® 8220, Dow Corning® 939, Dow Corning® 949, Dow Corning® 2-8194, all available from Dow Corning, Midland, Mich., and Silicone SM 253 available from General Electric, Waterford, N.Y.

"Hydrophobically modified polymer" and "Hydrophobically modified polyacrylamide" both mean a polyacrylamide as defined herein wherein a portion of the amido (—C(O)NH$_2$) groups along the polymer backbone is modified by transamidation with a hydrophobic amine. Accordingly, in addition to repeating units derived from anionic monomers the hydrophobically modified polymer or hydrophobically modified polyacrylamide comprises repeating units having the following structures where NRaRb represents the hydrophobic group resulting from transamidation with a hydrophobic amine and M is H or a base addition salt.

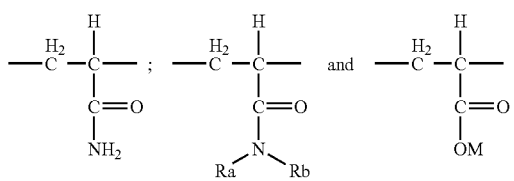

"Polyacrylamide" means a polymer formed by polymerization of acrylamide and one or more anionic monomers under free radical forming conditions. Polyacrylamides may additionally include non-ionic monomers. Suitable polyacrylamides are commercially available in emulsion, dispersion, solution and powder form or can be prepared by standard methods used for free radical polymerization of vinyl monomers.

"Cosmetically acceptable excipient" means a non-toxic, non-irritating substance which when mixed with the hydrophobically modified acrylamide or hydrophobically modified polymer of this invention makes the polyacrylamide/polymer more suitable to be applied to hair or skin.

Preferred Embodiments

In one embodiment, the hydrophobically modified polymer or hydrophobically modified polyacrylamide of this invention is prepared by transamidation of amido (—C(O)NH$_2$) groups of a anionic polyacrylamide with about 0.1 to about 10 mole percent of one or more hydrophobic amines by heating at elevated temperature and pressure. Base may be added to maintain the hydrophobic amine in its basic rather than protonated form. Suitable bases include ammonia and alkali and alkaline earth metal hydroxides and carbonates.

In another embodiment, the anionic polyacrylamide is mixed with an aqueous sulfite solution made from sodium metabisulfite and sodium hydroxide in a stainless steel pressure reactor at a pH of about 9-10. The hydrophobic amine is added, and the air in the reactor is replaced with nitrogen. The mixture is heated at about 120° C. to about 180° C. for about 0.5 to about 8 hours. In an embodiment, the mixture is heated at about 140° C. for about 5 hours. The resulting hydrophobically modified polymer or hydrophobically modified polyacrylamide is then diluted to the desired concentration with water and optionally treated with one or more preservatives at elevated temperature. In an embodiment, the hydrophobically modified polymer or hydrophobically modified polyacrylamide solution is treated with methyl paraben and propyl paraben at 85-90° C. for 1 hour. The product is characterized by viscometric, $^{13}$C NMR, GC, and GPC methods.

In another embodiment, the polyacrylamides are composed of at least about 50 mole percent acrylamide.

In another embodiment, the hydrophobically modified polyacrylamides have a weight average molecular weight of about 10,000 to 10,000,000.

In another embodiment, the polyacrylamides are modified by transamidation with about 0.1 to about 10 mole percent of one or more hydrophobic amines.

In another embodiment, the polyacrylamides are modified by transamidation with about 0.1 to about 50 mole percent of one or more hydrophobic amines.

In another embodiment, the anionic monomers are selected from the group consisting of: acrylic acid, 2-acrylamido-2-methylpropanesulfonic acid, and styrene sulfonic acid.

In another embodiment, the hydrophobic amines are selected from the group consisting of: $C_6$-$C_{22}$ alkyl amines and amino-functionalized silicones.

In another embodiment, the polyacrylamides are acrylamide/acrylic acid copolymers.

In another embodiment, the alkyl amines are selected from the group consisting of octylamine, dodecylamine, and hexadecylamine.

In another embodiment, the alkyl amines are selected from the group consisting of amino-functionalized silanes.

In another embodiment, the composition comprises about 0.01 to about 40 weight percent of hydrophobically modified polyacrylamides, based on actives.

In another embodiment, the hydrophobically modified polyacrylamides further comprise one or more non-ionic monomers.

In another embodiment, the nonionic monomers are selected from the group consisting of: methacrylamide; N,N-dimethylacrylamide; diacetoneacrylamide; acrylonitrile; N-vinylpyrrolidone; vinyl acetate; and allyl alcohol.

The compositions of the present disclosure may be utilized for various consumer and industrial purposes.

The compositions are selected from the group consisting of shampoos, aftershaves, sunscreens, lotions, hand and body creams, liquid soaps, bar soaps, bath oil bars, shaving creams, dishwashing liquids, detergents, surface cleaners, disposable wipes, conditioners, latex paints, permanent waves, hair relaxers, hair bleaches, hair detangling lotion, styling gel, styling glazes, spray foams, styling creams, styling waxes, styling lotions, mousses, spray gels, pomades, shower gels, bubble baths, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products, spritzes, styling waxes and balms.

The compositions encompassed by this invention may be cosmetically acceptable compositions.

In one embodiment, the composition contains one or more cosmetically acceptable excipients.

In an embodiment, the cosmetically acceptable excipients are selected from the group consisting of saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

Representative saccharides include nonionic or cationic saccharides such as agarose, amylopectins, amyloses, arabinans, arabinogalactans, arabinoxylens, carageenans, gum arabic, carboxymethyl guar gum, carboxymethyl(hydroxypropyl) guar gum, hydroxyethyl guar gum, carboxymethyl cellulose, cationic guar gum, cellulose ethers including methyl cellulose, chondroitins, chitins, chitosan, chitosan pyrrolidone carboxylate, chitosan glycolate chitosan lactate, cocodimonium hydroxypropyl oxyethyl cellulose, colominic acid (poly-N acetyl-neuraminic acid), corn starch, curdlan, dermatin sulfate, dextrans, furcellarans, dextrans, cross-linked dextrans, dextrin, emulsan, ethyl hydroxyethyl cellulose, flaxseed saccharide (acidic), galactoglucomannans, galactomannans, glucomannans, glycogens, guar gum, hydroxy ethyl starch, hydroxypropyl methyl cellulose, hydroxy ethyl cellulose, hydroxy propyl cellulose, hydroxypropyl starch, hydroxypropylated guar gums, gellan gum, gellan, gum ghatti, gum karaya, gum tragancanth (tragacanthin), heparin, hyaluronic acid, inulin, keratin sulfate, konjac mannan, modified starches, laminarans, laurdimonium hydroxypropyl oxyethyl cellulose, okra gum, oxidized starch, pectic acids, pectin, polydextrose, polyquaternium-4, polyquaternium-10, polyquaternium-28, potato starch, protopectins, psyllium seed gum, pullulan, sodium hyaluronate, starch diethylaminoethyl ether, starch hydroxypropyltrimoium chloride, hydroxyproyl starch phosphate, steardimonium hydroxyethyl cellulose, raffinose, rhamsan, tapioca starch, whelan, levan, scleroglucan, sodium alginate, stachylose, succinoglycan, wheat starch, xanthan gum, xylans, xyloglucans, and mixtures thereof. Microbial saccharides can be found in Kirk-Othmer *Encyclopedia of Chemical Technology*, Fourth Edition, Vol. 16, John Wiley and Sons, NY pp. 578-611 (1994) which is incorporated entirely by reference. Complex carbohydrates can be found in Kirk-Othmer *Encyclopedia of Chemical Technology*, Fourth Edition, Vol. 4, John Wiley and Sons, NY pp. 930-948, 1995 which is herein incorporated by reference.

The cosmetically acceptable composition of this invention may include surface-active agents. Surface active agents include surfactants, which typically provide detersive functionality to a formulation or act simply as wetting agents. Surface-active agents can generally be categorized as anionic surface-active agents, cationic surface-active agents, nonionic surface-active agents, amphoteric surface-active agents and zwitterionic surface-active agents.

Anionic surface-active agents useful herein include those disclosed in U.S. Pat. No. 5,573,709, incorporated herein by reference. Examples include alkyl and alkyl ether sulfates. Specific examples of alkyl ether sulfates which may be used In this invention are sodium and ammonium salts of lauryl sulfate, lauryl ether sulfate, coconut alkyl triethylene glycol ether sulfate; tallow alkyl triethylene glycol ether sulfate, and tallow alkyl hexaoxyethylene sulfate. Preferred alkyl ether sulfates are those comprising a mixture of individual compounds, said mixture having an average alkyl chain length of from about 12 to about 16 carbon atoms and an average degree of ethoxylation of from about 1 to about 6 moles of ethylene oxide.

Another suitable class of anionic surface-active agents is the alkyl sulfuric acid salts. Important examples are the salts of an organic sulfuric acid reaction product of a hydrocarbon of the methane series, including iso-, neo-, ineso-, and n-paraffins, having about 8 to about 24 carbon atoms, preferably about 12 to about 18 carbon atoms and a sulfonating agent, e.g., $SO_3$, $H_2SO_4$, oleum, obtained according to known sulfonation methods, including bleaching and hydrolysis. Preferred are alkali metal and ammonium sulfated $C_{12-38}$ n-paraffins.

Additional synthetic anionic surface-active agents include the olefin sulfonates, the beta-alkyloxy alkane sulfonates, and the reaction products of fatty acids esterified with isethionic acid and neutralized with sodium hydroxide, as well as succinamates. Specific examples of succinamates include disodium N-octadecyl sulfosuccinanrate; tetrasodium N-(1,2-dicarboxyethyl)-N-octadecylsulfosuccinamate; diamyl ester of sodium sulfosuccinic acid; dihexyl ester of sodium sulfosuccinic acid; dioctyl esters of sodium sulfosuccinic acid.

Preferred anionic surface-active agents for use in the cosmetically acceptable composition of this invention include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric mono glyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric surface-active agents which may be used in the cosmetically acceptable composition of this invention include derivatives of aliphatic secondary and tertiary amines, in which the aliphatic substituent contains from about 8 to 18 carbon atoms and an anionic water solubilizing group e.g., carboxy, sulfonate, sulfate, phosphate, or phosphonate. Representative examples include sodium 3-dodecyl-aminopropionate, sodium 3-dodecylaminopropane sulfonate, sodium lauryl sarcosinate, N-alkyltaurines such as the one prepared by reacting dodecylamine with sodium isethionate as described in U.S. Pat. No. 2,658,072, N-higher alkyl aspartic acids as described in U.S. Pat. No. 2,438,091, and the products sold under the trade name MIRANOL™ as described in U.S. Pat. No. 2,528,378. Other sarcosinates and sarcosinate derivatives can be found in the CTFA Cosmetic Ingredient Handbook, Fifth Edition, 1988, page 42 incorporated herein by reference.

Cationic surface-active agents generally include, but are not limited to fatty quaternary ammonium compounds containing from about 8 to about 18 carbon atoms. The anion of the quaternary ammonium compound can be a common ion such as chloride, ethosulfate, methosulfate, acetate, bromide, lactate, nitrate, phosphate, or tosylate and mixtures thereof. The long chain alkyl groups can include additional or replaced carbon or hydrogen atoms or ether linkages. Other substitutions on the quaternary nitrogen can be hydrogen, hydrogen, benzyl or short chain alkyl or hydroxyalkyl groups such as methyl, ethyl, hydroxymethyl or hydroxyethyl, hydroxypropyl or combinations thereof. The structure or representative quaternary ammonium compounds is provided in the CTFA Cosmetic Ingredient Handbook, Fifth Edition, 1988, page 40.

Examples of quaternary ammonium compounds include but are not limited to: behentrimonium chloride, cocotrimonium chloride, cethethyldimonium bromide, dibehenyldimonium chloride, dihydrogenated tallow benzylmonium chloride, disoyadimonium chloride, ditallowedimonium chloride, hydroxycetyl hydroxyethyl dimonium chloride, hydroxyethyl behenamidopropyl dimonium chloride, hydroxyethyl cetyldimonium chloride, hydroxyethyl tallowedimonium chloride, myristalkonium chloride, PEG-2 oleamonium chloride, PEG-5 stearmonium chloride, PEG-15 cocoyl quaternium 4, PEG-2 stearalkonium 4, lauryltrimonium chloride; Quaternium-16; Quaternium-18, lauralkonium chloride, olealkmonium chloride, cetylpyridinium chloride, Polyquaternium-5, Polyquaternium-6, Polyquaternium-7, Polyquaternium-10, Polyquaternium-22, Polyquaternium-37, Polyquaternium-39, Polyquaternium-47, polyquaternium-55, cetyl trimonium chloride, dilauryldimonium chloride, cetalkonium chloride, dicetyldimonium chloride, soyatrimonium chloride, stearyl octyl dimonium methosulfate, and mixtures thereof. Other quaternary ammonium compounds are listed in the CTFA Cosmetic Ingredient Handbook, First Edition, on pages 41-42, incorporated herein by reference.

The cosmetically acceptable compositions may include di-long chain amines from about $C_{10}$ to $C_{22}$, long chain fatty amines from about $C_{10}$ to $C_{22}$, and mixtures thereof. Specific examples include dipalmitylamine, lauramidopropyldimethyl, stearamidopropyl dimethylamine.

The cosmetically acceptable compositions of this invention may also include fatty alcohols (typically monohydric alcohols), ethoxylated fatty alcohols, and di-tail phospholipids, which can be used to stabilize emulsion or dispersion forms of the cosmetically acceptable compositions. They also provide a cosmetically acceptable viscosity. Selection of the fatty alcohol is not critical, although those alcohols characterized as having fatty chains of $C_{10}$ to $C_{32}$, preferably $C_{14}$ to $C_{22}$, which are substantially saturated alkanols will generally be employed. Examples include stearyl alcohol, cetyl alcohol, cetostearyl alcohol, myristyl alcohol, behenyl alcohol, arachidic alcohol, isostearyl alcohol, and isocetyl alcohol. Cetyl alcohol is preferred and may be used alone or in combination with other fatty alcohols, preferably with stearyl alcohol. When used, the fatty alcohol is preferably included in the formulations of this invention at a concentration within the range from about 1 to about 8 weight percent, more preferably about 2 to about 6 weight percent. The fatty alcohols may also be ethoxylated. Specific examples include cetereth-20, steareth-20, steareth-21, and mixtures thereof. Phospholipids such as phosphatidylserine and phosphatidylcholine, and mixtures thereof may also be included.

Nonionic surface-active agents, which can be used in the cosmetically acceptable composition of this invention include those broadly defined as compounds produced by the condensation of alkylene oxide groups (hydrophilic in nature) with an organic hydrophobic compound, which may be aliphatic or alkyl aromatic in nature. Examples of preferred classes of nonionic surface-active agents are: the long chain alkanolamides; the polyethylene oxide condensates of alkyl phenols; the condensation product of aliphatic alcohols having from about 8 to about 18 carbon atoms, in either straight chain or branched chain configuration, with ethylene oxide; the long chain tertiary amine oxides; the long chain tertiary phosphine oxides; the long chain dialkyl sulfoxides containing one short chain alkyl or hydroxy alkyl radical of from about 1 to about 3 carbon atoms; and the alkyl polysaccharide (APS) surfactants such as the alkyl polyglycosides; the polyethylene glycol (PEG) glyceryl fatty esters.

Zwitterionic surface-active agents such as betaines can also be useful in the cosmetically acceptable composition of this invention. Examples of betaines useful herein include the high alkyl betaines, such as coco dimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, and lauryl bis-(2-hydroxypropyl)alpha-carboxyethyl betaine. The sulfobetaines may be represented by coco dimethyl sulfopropyl betaine, stearyl dimethyl sulfopropyl betaine, lauryl dimethyl sulfoethyl betaine, lauryl bis-(2-hydroxyethyl) sulfopropyl betaine and the like; amidobetaines and amidosulfobetaines, wherein the RCONH $(CH_2)_3$ radical is attached to the nitrogen atom of the betaine are also useful in this invention.

The anionic, cationic, nonionic, amphoteric or zwitterionic surface-active agents used in the cosmetically acceptable composition of this invention are typically used in an amount from about 0.1 to 50 percent by weight, preferably from about 0.5 to about 40 percent by weight, more preferably from about 1 to about 20 percent by weight.

The cosmetically acceptable composition of this invention may include humectants, which act as hygroscopic agents, increasing the amount of water absorbed, held and retained. Suitable humectants for the formulations of this invention include but are not limited to: acetamide MEA, ammonium lactate, chitosan and its derivatives, colloidal oatmeal, galactoarabinan, glucose glutamate, glerecyth-7, glygeryth-12, glycereth-26, glyceryth-31, glycerin, lactamide MEA, lactamide DEA, lactic acid, methyl gluceth-10, methyl gluceth-20, panthenol, propylene glycol, sorbitol, polyethylene glycol, 1,3-butanediol, 1,2,6-hexanetriol, hydrogenated starch hydrolysate, inositol, mannitol, PEG-5 pentaerythritol ether, polyglyceryl sorbitol, xylitol, sucrose, sodium hyaluronate, sodium PCA, and combinations thereof. Glycerin is a particularly preferred humectant. The humectant is present in the composition at concentrations of from about 0.5 to about 40 percent by weight, preferably from about 0.5 to about 20 percent by weight and more preferably from about 0.5 to about 12 percent by weight.

The cosmetically acceptable composition of this invention may include petrolatum or mineral oil components, which when selected will generally be USP or NF grade. The petrolatum may be white or yellow. The viscosity or consistency grade of petrolatum is not narrowly critical. Petrolatum can be partially replaced with mixtures of hydrocarbon materials, which can be formulated to resemble petrolatum in appearance and consistency. For example, mixtures of petrolatum or mineral oil with different waxes and the like may be combined. Preferred waxes include bayberry wax, candelilla wax, ceresin, jojoba butter, lanolin wax, montan wax, ozokerite, polyglyceryl-3-beeswax, polyglyceryl-6-pentastearate, microcrystalline wax, paraffin wax, isoparaffin, vaseline solid paraffin, squalene, oligomer olefins, beeswax, synthetic candelilla wax, synthetic carnauba, sythetic beeswax and the like may be blended together. Alkylmethyl siloxanes with varying degrees of substitution can be used to increase water retained by the skin. Siloxanes such as stearyl dimethicone, known as 2503 Wax, C30-45 alkyl methicone, known as AMS-C30 wax, and stearoxytrimethylsilane (and) stearyl alcohol, known as 580 Wax, each available from Dow Corning®, Midland, Mich., USA. Additional alkyl and phenyl silicones may be employed to enhance moisturizing properties. Resins such as dimethicone (and) trimethylsiloxysilicate, known as Dow Corning® 593 or cyclomethicone (and) trimethylsiloxysilicate, known as Dow Corning® 749 fluid, may be utilized to enhance film formation of skin care products. When used, the petrolatum, wax or hydrocarbon or oil component is included in the formulations at a concentration of about 1 to about 20 weight percent, more preferably about 1 to about 12 weight percent. When used, the silicone resins can be included from about 0.1 to about 10.0 weight percent.

Emollients are defined as agents that help maintain the soft, smooth, and pliable appearance of skin. Emollients function by their ability to remain on the skin surface or in the stratum corneum. The cosmetically acceptable composition of this invention may include fatty ester emollients, which are listed in the International Cosmetic Ingredient Dictionary, Eighth Edition, 2000, p. 1768 to 1773. Specific examples of suitable fatty esters for use in the formulation of this invention include isopropyl myristate, isopropyl palmitate, caprylic/capric triglycerides, cetyl lactate, cetyl palmitate, hydrogenated castor oil, glyceryl esters, hydroxycetyl isostearate, hydroxy cetyl phosphate, isopropyl isostearate, isostearyl isostearate, diisopropyl sebacate, PPG-5-Ceteth-20, 2-ethylhexyl isononoate, 2-ethylhexyl stearate, $C_{12}$ to $C_{16}$ fatty alcohol lactate, isopropyl lanolate, 2-ethyl-hexyl salicylate, and mixtures thereof. The presently preferred fatty esters are isopropyl myristate, isopropyl palmitate, PPG-5-Ceteth-20, and caprylic/capric triglycerides. When used the fatty ester emollient is preferably included in the formulations of this invention at a concentration of about 1 to about 8 weight percent, more preferably about 2 to about 5 weight percent.

The compositions of this invention may also include silicone compounds. Preferably, the viscosity of the silicone component at a temperature of 25° C. is from about 0.5 to about 12,500 cps. Examples of suitable materials are dimethylpolysiloxane, diethylpolysiloxane, dimethylpolysiloxane-diphenylpolysiloxane, cyclomethicone, trimethylpolysiloxane, diphenylpolysiloxane, and mixtures thereof. Dimethicone, a dimethylpolysiloxane endblocked with trimethyl units, is one preferred example. Dimethicone having a viscosity between 50 and 1,000 cps is particularly preferred. When used, the silicone oils are preferably included in the formulations of this invention at a concentration of 0.1 to 5 weight percent, more preferably 1 to 2 weight percent.

The cosmetically acceptable compositions of this invention may include volatile and non-volatile silicone oils or fluids. The silicone compounds can be either linear or cyclic polydimethylsiloxanes with a viscosity from about 0.5 to about 100 centistokes. The most preferred linear polydimethylsiloxane compounds have a range from about 0.5 to about 50 centistokes. One example of a linear, low molecular weight, volatile polydimethylsiloxane is octamethyltrisiloxane, available under the trade name Dow Corning® 200 fluid having a viscosity of about 1 centistoke. When used, the silicone oils are preferably included in the formulations of this invention at a concentration of 0.1 to 30 weight percent, more preferably 1 to 20 weight percent.

The cosmetically acceptable compositions of this invention may include volatile, cyclic, low molecular weight polydimethylsiloxanes (cyclomethicones). The preferred cyclic volatile siloxanes can be polydimethyl cyclosiloxanes having an average repeat unit of 4 to 6, and a viscosity from about 2.0 to about 7.0 centistokes, and mixtures thereof. Preferred cyclomethicones are available from Dow Corning, Midland, Mich., USA under the trade names Dow Corning® 244 fluid, Dow Corning® 245 fluid, Dow Corning® 246, Dow Corning® 344 fluid and Dow Corning® 345 fluid, and Silicone SF-1173 and Silicone SF-1202 from General Electric, Waterford, N.Y., USA. When used, the silicone oils are preferably included in the formulations of this invention at a concentration of 0.1 to 30 weight percent, more preferably 1 to 20 weight percent.

Silicone surfactants or emulsifiers with polyoxyethylene or polyoxypropylene side chains may also be used in compositions of the current invention. Preferred examples include dimethicone copolyols, Dow Corning® 3225C and 5225C Formulation Aids, available from Dow Corning, Midland, Mich., USA and Silicone SF-1528, available from General Electric, Waterford, N.Y., USA. The side chains may also include alkyl groups such as lauryl or cetyl. Preferred are lauryl methicone copolyol, known as Dow Corning® 5200 Formulation Aid, and cetyl dimethicone copolyol, known as Abil EM-90, available from Goldschmidt Chemical Corporation, Hopewell, Va. Also preferred is lauryl dimethicone, known as Belsil LDM 3107 VP, available from Wacker-Chemie, Munchen, GER. When used, the silicone surfactants are preferably included in the formulations of this invention at a concentration of 0.1 to 30 weight percent, more preferably 1 to 15 weight percent.

Amine functional silicones and emulsions may be utilized in the present invention. Preferred examples include Dow Corning® 8220, Dow Corning® 939, Dow Corning® 949, Dow Corning® 2-8194, all available from Dow Corning, Midland, Mich., USA. Also preferred is Silicone SM 253 available from General Electric, Waterford, N.Y., USA. When used, the amine functional silicones are preferably included in the formulations of this invention at a concentration of 0.1 to 5 weight percent, more preferably 0.1 to 2.0 weight percent.

The cosmetically acceptable compositions of this invention may include volatile hydrocarbon oils. The volatile hydrocarbon comprises about $C_6$ to $C_{22}$ atoms. A preferred volatile hydrocarbon is an aliphatic hydrocarbon having a chain length of about $C_6$ to $C_{16}$ carbon atoms. An example of such compound includes isohexadecane, under the tradename Permethyl 101A, available from Presperse, South Plainfield, N.J., USA. Another example of a preferred volatile hydrocarbon is $C_{12}$ to $C_{14}$ isoparaffin, under the tradename Isopar M, available from Exxon, Baytown, Tex., USA. When used, the volatile hydrocarbons are preferably included in the formulations of this invention at a concentration of 0.1 to 30 weight percent, more preferably 1 to 20 weight percent.

The cosmetically acceptable compositions of this invention may include cationic and ampholytic conditioning polymers. Examples of such include, but are not limited to those listed by the International Cosmetic Ingredient Dictionary published by the Cosmetic, Toiletry, and Fragrance Association (CTFA), 1101 17$^{th}$ Street, N.W., Suite 300, Washington, D.C. 20036. General examples include quaternary derivatives of cellulose ethers, quaternary derivatives of guar, homopolymers and copolymers of DADMAC, homopolymers and copolymers of MAPTAC and quaternary derivatives of starches. Specific examples, using the CTFA designation, include, but are not limited to Polyquaternium-10, Guar hydroxypropyltrimonium chloride, Starch hydroxypropyltrimonium chloride, Polyquaternium-4, Polyquaternium-5, Polyquaternium-6, Polyquaternium-7, Polyquaternium-14, Polyquaternium-15, Polyquaternium-22, Polyquaternium-24, Polyquaternium-28, Polyquaternium-32, Polyquaternium-33, Polyquaternium-36, Polyquaternium-37, Polyquaternium-39, Polyquaternium-45, Polyquaternium-47 and polymethacrylamidopropyltrimonium chloride, Polyquaternium-55 and mixtures thereof. When used, the conditioning polymers are preferably included in the cosmetically acceptable composition of this invention at a concentration of from 0.1 to 10 weight percent, preferably from 0.2 to 6 weight percent and most preferably from 0.2 to 5 weight percent.

The cosmetically acceptable composition of this invention may include one or more rheological modifiers. The rheological modifiers which can be used in this invention include, but are not limited to high molecular weight crosslinked homopolymers of acrylic acid, and Acrylates/C10-30 Alkyl Acrylate Crosspolymer, such as the Carbopol® and Pemulen® series, both available from Noveon, Inc., Cleveland, Ohio, USA; anionic acrylate polymers such as Salcare® AST and cationic acrylate polymers such as Salcare® SC96, available from Ciba Specialties, High Point, N.C., USA; acrylamidopropylttrimonium chloride/acrylamide; hydroxyethyl methacrylate polymers, Steareth-10 Allyl Ether/Acrylate Copolymer; Acrylates/Beheneth-25 Metacrylate Copolymer, known as Aculyn® 28, available from Rohm and Haas/International Specialties, Wayne, N.J., USA; glyceryl polymethacrylate, Acrylates/Steareth-20 Methacrylate Copolymer; bentonite; gums such as alginates, carageenans, gum acacia, gum arabic, gum ghatti, gum karaya, gum tragacanth, guar gum; guar hydroxypropyltrimonium chloride, xanthan gum or gellan gum; cellulose derivatives such as sodium carboxymethyl cellulose, hydroxyethyl cellulose, hydroxymethyl carboxyethyl cellulose, hydroxymethyl carboxypropyl cellulose, ethyl cellulose, sulfated cellulose, hydroxypropyl cellulose, methyl cellulose, hydroxypropylmethyl cellulose, microcrystalline cellulose; agar; pectin; gelatin; starch and its derivatives; chitosan and its derivatives such as hydroxyethyl chitosan; polyvinyl alcohol, PVM/MA copolymer, PVM/MA decadiene crosspolymer, poly(ethylene oxide) based thickeners, sodium carbomer, and mixtures thereof. When used, the rheology modifiers are preferably included in the cosmetically acceptable composition of this invention at a concentration of from 0.01 to 12 weight percent, preferably from 0.05 to 10 weight percent and most preferably from 0.1 to 6 weight percent.

The cosmetically acceptable composition of this invention may include one or more antioxidants, which include, but are not limited to ascorbic acid, BHT, BHA, erythorbic acid, bisulfite, thioglycolate, tocopherol, sodium metabisulfite, vitamin E acetate, and ascorbyl palmitate. The antioxidants will be present at from 0.01 to 5 weight percent, preferably 0.1 to 3 weight percent and most preferably from 0.2 to 2 weight percent of the cosmetically acceptable composition.

The cosmetically acceptable composition of this invention may include one or more sunscreen active agents. Examples of sunscreen active agents include, but are not limited to octyl methoxycinnamate (ethylhexyl p-methoxycinnamate), octyl salicylate oxybenzone (benzophenone-3), benzophenone-4, menthyl anthranilate, dioxybenzone, aminobenzoic acid, amyl dimethyl PABA, diethanolamine p-methoxy cinnamate, ethyl 4-bis(hydroxypropyl)aminobenzoate, 2-ethylhexyl-2-cyano-3,3-diphenylacrylate, homomethyl salicylate, glyceryl aminobenzoate, dihydroxyacetone, octyl dimethyl PABA, 2-phenylbenzimidazole-5-sulfonic acid, triethanolamine salicylate, zinc oxide, and titanium oxide, and mixtures thereof. The amount of sunscreen used in the cosmetically acceptable composition of this invention will vary depending on the specific UV absorption wavelength(s) of the specific sunscreen active(s) used and can be from 0.1 to 10 percent by weight, from 2 to 8 percent by weight.

The cosmetically acceptable composition of this invention may include one or more preservatives. Examples of preservatives include, but are not limited to, 1,2-dibromo-2,4-dicyano butane (Methyldibromo Glutaronitrile, known as MERGUARD®, Nalco Company, Naperville, Ill., USA), benzyl alcohol, imidazolidinyl urea, 1,3-bis(hydroxymethyl)-5,5-dimethyl-2,3-imidazolidinedione (e.g., DMDM Hydantoin, known as GLYDANT®, Lonza, Fairlawn, N.J., USA.), methylchloroisothiazolinone and methylisothiazolinone (e.g., Kathon®, Rohm & Haas Co., Philadelphia, Pa., USA), methyl paraben, propyl paraben, phenoxyethanol, and sodium benzoate, and mixtures thereof.

The cosmetically acceptable composition of this invention may include any other ingredient normally used in cosmetics. Examples of such ingredients include, but are not limited to, buffering agents, fragrance ingredients, chelating agents, color additives or dyestuffs which can serve to color the composition itself or keratin, sequestering agents, softeners, foam synergistic agents, foam stabilizers, sun filters, UV-absorbers, and peptizing agents.

The surface of pigments, such titanium dioxide, zinc oxide, talc, calcium carbonate or kaolin, can be treated with the anionic polymer described herein and then used in the cosmetically acceptable composition of this invention. The treated pigments are then more effective as sunscreen actives and for use in color cosmetics such as make up and mascara.

The cosmetically acceptable composition of this invention may contain water and also any cosmetically acceptable solvent. Examples of acceptable solvents include, but are not limited to monoalcohols, such as alkanols having 1 to 8 carbon atoms (like ethanol, isopropanol, benzyl alcohol and phenylethyl alcohol) polyalcohols, such as alkylene glycols (like glycerine, ethylene glycol and propylene glycol) and glycol ethers, such as mono-, di- and tri-ethylene glycol monoalkyl ethers, for example ethylene glycol monomethyl ether and diethylene glycol monomethyl ether, used singly or in a mixture. These solvents can be present in proportions of up to as much as 70 percent by weight, for example from 0.1 to 70 percent by weight, relative to the weight of the total composition.

The cosmetically acceptable composition of this invention also can contain electrolytes, such as aluminum chlorohydrate, alkali metal salts, e.g., sodium, potassium or lithium salts, these salts preferably being halides, such as the chloride or bromide, and the sulfate, or salts with organic acids, such as the acetates or lactates, and also alkaline earth metal salts, preferably the carbonates, silicates, nitrates, acetates, gluconates, pantothenates and lactates of calcium, magnesium and strontium.

Compositions for treating skin include aftershaves, sunscreens, lotions, hand and body creams, liquid soaps, bar soaps, bath oil bars, shaving creams, dishwashing liquids, shower gels, bubble baths, and the like.

The skin care compositions of this invention may be prepared as either oil-in-water, water-in-oil emulsions, triple emulsions, or dispersions.

Preferred oil-in-water emulsions are prepared by first forming an aqueous mixture of the water-soluble components, e.g. unsaturated quaternary ammonium compounds, the humectant, water-soluble preservatives, followed by adding water-insoluble components. The water-insoluble components include the emulsifier, water-insoluble preservatives, petrolatum or mineral oil component, fatty alcohol component, fatty ester emollient, and silicone oil component. The input of mixing energy will be high and will be maintained for a time sufficient to form a water-in-oil emulsion having a smooth appearance (indicating the presence of relatively small micelles in the emulsion). Preferred dispersions are generally prepared by forming an aqueous mixture of the water-soluble components, followed by addition of thickener with suspension power for water-insoluble materials.

The cosmetically acceptable composition of this invention can also be packaged as an aerosol, in which case it can be applied either in the form of an aerosol spray or in the form of an aerosol foam. As the propellant gas for these aerosols, it is possible to use, in particular, dimethyl ether, carbon dioxide, nitrogen, nitrous oxide, air and volatile hydrocarbons, such as butane, isobutane, and propane.

Compositions for treating hair include bath preparations such as bubble baths, soaps, and oils, shampoos, conditioners, hair bleaches, hair coloring preparations, temporary and permanent hair colors, color conditioners, hair lighteners, coloring and non-coloring hair rinses, hair tints, hair wave sets, permanent waves, curling, hair straighteners, hair grooming aids, hair tonics, hair dressings and oxidative products. The hydrophobically modified polyacrylamides or hydrophobically modified polymers may also be utilized in styling type leave-in products such as gels, mousses, spritzes, styling creams, styling waxes, pomades, balms, and the like, either alone or in combination with other polymers or structuring agents in order to provide control and hair manageability with a clean, natural, non-sticky feel.

Hair care compositions of this invention give slippery feel and that can be easily rinsed from the hair due to the presence of the hydrophobically modified polyacrylamides or hydrophobically modified polymers, volatile silicones, other polymers, surfactants or other compounds that may alter the deposition of materials upon the hair.

In the case of cleansing formulations such as a shampoo for washing the hair, or a liquid hand soap, or shower gel for washing the skin, the compositions contain anionic, cationic, nonionic, zwitterionic or amphoteric surface-active agents typically in an amount from about 3 to about 50 percent by weight, preferably from about 3 to about 20 percent, and their pH is general in the range from about 3 to about 10.

Preferred shampoos of this invention contain combinations of anionic surfactants with zwitterionic surfactants and/or amphoteric surfactants. Especially preferred shampoos contain from about 0 to about 16 percent active of alkyl sulfates, from 0 to about 50 weight percent of ethoxylated alkyl sulfates, and from 0 to about 50 weight percent of optional surface-active agents selected from the nonionic, amphoteric, and zwitterionic surface-active agents, with at least 5 weight percent of either alkyl sulfate, ethoxylated alkyl sulfate, or a mixture thereof, and a total surfactant level of from about 10 weight to about 25 percent.

The shampoo for washing hair also can contain other conditioning additives such as silicones and conditioning polymers typically used in shampoos. U.S. Pat. No. 5,573,709 provides a list of non-volatile silicone conditioning agents that can be used in shampoos. The conditioning polymers for use with the present invention are listed in the Cosmetic, Toiletries and Fragrance Associations (CTFA) dictionary. Specific examples include the Polyquaterniums (example Polyquaternium-1 to Polyquaternium-53), guar hydroxypropyl trimonium chloride, starch hydroxypropyl trimonium chloride and polymethacrylamidopropyl yrimonium chloride.

Other preferred embodiments consist of use in the form of a rinsing lotion to be applied mainly before or after shampooing. These lotions typically are aqueous or aqueous-alcoholic solutions, emulsions, thickened lotions or gels. If the compositions are presented in the form of an emulsion, they can be nonionic, anionic or cationic. The nonionic emulsions consist mainly of a mixture of oil and/or a fatty alcohol with a polyoxyethyleneated alcohol, such as polyoxyethyleneated stearyl or cetyl/stearyl alcohol, and cationic surface-active agents can be added to these compositions. The anionic emulsions are formed essentially from soap.

If the compositions are presented in the form of a thickened lotion or a gel, they contain thickeners in the presence or absence of a solvent. The thickeners which can be used are especially resins, acrylic acid thickeners available from B.F. Goodrich; xanthan gums; sodium alginates; gum arabic; cellulose derivatives and poly(ethylene oxide) based thickeners, and it is also possible to achieve thickening by means of a mixture of polyethylene glycol stearate or distearate or by means of a mixture of a phosphoric acid ester and an amide.

The concentration of thickener is generally 0.05 to 15 percent by weight. If the compositions are presented in the form of a styling lotion, shaping lotion, or setting lotion, they generally comprise, in aqueous, alcoholic or aqueous-alcoholic solution, the ampholyte polymers defined above.

In the case of hair fixatives, the composition may also contain one or more additional hair fixative polymers. When present, the additional hair fixative polymers are present in a total amount of from about 0.25 to about 10 percent by weight. The additional hair fixative resin can be selected from the following group as long as it is compatible with a given polymer: acrylamide copolymer, acrylamide/sodium acrylate copolymer, acrylate/ammonium methacrylate copolymer, an acrylate copolymer, an acrylic/acrylate copolymer, adipic acid/dimethylaminohydroxypropyl diethylenetriamine copolymer, adipic acid/epoxypropyl diethylenetriamine copolymer, allyl stearate/VA copolymer, aminoethylacrylate phosphate/acrylate copolymer, an ammonium acrylate copolymer, an ammonium vinyl acetate/acrylate copolymer, an AMP acrylate/diacetoneacrylamide copolymer, an AMPD acrylate/diacetoneacrylamide copolymer, butyl ester of ethylene/maleic anhydride copolymer, butyl ester of PVM/MA copolymer, calcium/sodium PVM/MA copolymer, corn starch/acrylamide/sodium acrylate copolymer, diethylene glycolamine/epichlorohydrin/piperazine-copolymer, dodecanedioic acid/cetearyl alcohol/glycol copolymer, ethyl ester of PVM/MA copolymer, isopropyl ester of PVM/MA copolymer, karaya gum, a methacryloyl ethyl betaine/methacrylate copolymer, an octylacrylamide/acrylate/butylaminoethyl methacrylate copolymer, an octylacrylamide/acrylate copolymer, phthalic anhydride/glycerin/glycidyl decanoate copolymer, a phthalic/trimellitic/glycol copolymer, polyacrylamide, polyacrylamidomethylpropane sulfonic acid, polybutylene terephthalate, polyethylacrylate, polyethylene, polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-39, polyquaternium-47, polyvinyl acetate, polyvinyl butyral, polyvinyl imidazolinium acetate, polyvinyl methyl ether, PVM/MA copolymer, PVP, PVP/dimethylaminoethylmethacrylate copolymer, PVP/eicosene copolymer, PVP/ethyl methacrylate/methacrylic acid copolymer, PVP/hexadecene copolymer, PVP/VA copolymer, PVP/vinyl acetate/itaconic acid copolymer, shellac, sodium acrylates copolymer, sodium acrylates/Acrylnitrogens copolymer, sodium acrylate/vinyl alcohol copolymer, sodium carrageenan, starch diethylaminoethyl ether, stearylvinyl ether/maleic anhydride copolymer, sucrose benzoate/sucrose acetate isobutyrate/butyl benzyl phthalate copolymer, sucrose benzoate/sucrose acetate isobutyrate/butyl benzyl phthalate/methyl methacrylate copolymer, sucrose benzoate/sucrose acetate isobutyrate copolymer, a vinyl acetate/crotonate copolymer, vinyl acetate/crotonic acid copolymer, vinyl acetate/crotonic acid/methacryloxybenzophenone-1 copolymer, vinyl acetate/crotonic acid/vinyl neodecanoate copolymer, and mixtures thereof. Synthetic polymers used for creating styling aids are described in "The History of Polymers in Haircare," Cosmetics and Toiletries, 103 (1988), incorporated herein by reference. Other synthetic polymers that may be used with the present invention can be referenced in the CTFA Dictionary, Fifth Edition, 2000, incorporated herein by reference.

If the compositions of the instant invention are intended for use in the dyeing of keratin fibers, and in particular human hair, they generally contain at least one oxidation dyestuff precursor and/or one direct dyestuff, in addition to the hydrophobically modified polymer or hydrophobically modified polyacrylamide. They also can contain any other adjuvant normally used in this type of composition.

The pH of the dyeing compositions is generally 7 to 11 and can be adjusted to the desired value by adding an alkalizing agent.

The compositions according to this invention also can be used for waving or straightening the hair. In this case, the composition generally contains, in addition to the hydrophobically modified polymer or hydrophobically modified acrylamide, one or more reducing agents and, if appropriate, other adjuvants normally used in this type of composition; such compositions are intended for use conjointly with a neutralizing composition.

The compositions encompassed by this invention may be applied to various types of substrates.

In one embodiment, the substrate is a household surface or an industrial surface.

In another embodiment, the substrate is selected from the group consisting of: hair, skin, nails, a keratin containing substrate, a hard surface, a carpet, a fabric, wood, a plastic containing composition, and vinyl.

EXAMPLES

Example 1

Modification of Acrylamide-Sodium Acrylate Copolymer with Dodecylamine

To a Parr reactor is added an aqueous solution of acrylamide-sodium acrylate copolymer-solution (70:30 mole percent, 12 percent polymer actives, 291.7 g), a mixture of aqueous sodium hydroxide solution (50%, 1.8 g) and aqueous sodium metabisulfite solution (15%, 14.9 g) and deionized water (40.7 g). Finely ground dodecylamine is then added and the mixture is thoroughly stirred. The reactor is then sealed, the stirring is set to the maximum setting and the reactor is pressurized with nitrogen and vented (repeat five times). The reactor is then sealed, heated to 140° C. and maintained at 140° C. for five hours. The modified polymer solution is cooled to 90° C. at which time a mixture of methyl paraben (0.4 g), propyl paraben (0.1 g) and deionized water (20 g) pre-heated to 90° C. is added to the hot polymer solution. The mixture is stirred for one hour and then cooled to ambient temperature to provide the hydrophobically modified polymer or hydrophobically modified polyacrylamide solution.

Example 2

Foaming

The evaluation of foaming property of hydrophobically modified polyacrylamide or hydrophobically modified polymeric surfactants was done using the Hart DeGeorge Test method. The method uses a blender to generate the foam. The foam produced is thick and creamy and similar to the foam in practical use of rinse off products. The shampoo solution is agitated in a blender for one minute. The foam is then poured into a funnel placed on a sieve with a #20 mesh screen. A gauging wire is placed 80 mm from the bottom of the funnel. The time for the level of foam to reach the wire (seconds) is recorded; the higher the number, the better the foam.

Table 1 lists the shampoo base formulation used for the foam evaluation. Polymeric surfactant or benchmark was added in the ingredient called "polymer" at 0.5% or 1.0% actives.

The foaming evaluation is summarized in Table 2.

TABLE 1

| Shampoo Base | | |
|---|---|---|
| INCI (International Nomenclature for Cosmetic Ingedients) | Ingredient Concentration % | Wt. % Ingredient in Formula |
| Water | | 35.0 |
| Sodium lauryl sulfate | 30 | 20.0 |
| Sodium lauryl ether sulfate | 30 | 20.0 |
| Cocamidopropyl betaine | 30 | 3.0 |
| Lauramide DEA | 100 | 3.0 |
| Citric acid | 100 | 0.3 |
| Sodium Chloride | 100 | 1.0 |
| Polymer | | 0.5 or 1.0 (active) |
| Disodium EDTA | 100 | 0.1 |
| DMDM Hydantoin | 55 | 0.1 |
| Water | | Qs |
| pH adjustment | 50 | |

TABLE 2

| Hart DeGeorge Foam Evaluation | | |
|---|---|---|
| Sample Name | Drainage Time (S) | |
| Polymer Level (active) | 0.50% | 1.00% |
| Control (Shampoo without polymer) | 13.7 | 13.7 |
| Nalco Polymeric Surfactant (5605-192) | 21 | 26.7 |

It is clear that Nalco's polymeric surfactant (5605-192) almost doubled foam performance compared to the control.

Example 2

Surface Tension/Wetting Properties

Surface tension, a tool to evaluate wetting properties, was also measured. A mixture solution of polymeric surfactant and common surfactants was prepared at a 3/17 ratio in an active base and diluted with water to 0.6%. The surface tension was tested on a surface tension instrument (Kress Processor Tensiometer K-12) and average from 5 replicates was reported in table 3. Table 3 shows the test result.

TABLE 3

| Surface Tension Measurement | | |
|---|---|---|
| Sample Name | Surface Tension (mN/cm) | Standard Deviation |
| Water | 72.05 | 0.00994 |
| SLES/Cocamidopropyl betaine | 30.94 | 0.01091 |
| SLES/Nalco polymeric Surfactant (5605-192) | 32.42 | 0.09029 |

It is clear that polymeric surfactant (5605-192) has comparable surface tension to the benchmark (cocamidopropyl betaine) which is used commonly to boost foam.

We claim:

1. A method of removing residue, dirt, and grime from a substrate, a household surface, or an industrial surface, the method comprising: applying to the substrate, the household surface, or the industrial surface a composition comprising one or more polyacrylamides, wherein the polyacrylamides are hydrophobically modified by transamidation and contain acrylamide and one or more anionic monomers and excludes a cationic monomer then rinsing the composition off the substrate, household surface, or industrial surface to remove undesirable residues, dirt, and grime from the substrate, household surface, or industrial surface.

2. The method of claim 1 wherein said substrate, household surface or industrial surface is selected from the group consisting of: hair, skin, nails, a keratin containing substrate, a hard surface, a carpet, a fabric, wood, a plastic containing composition, and vinyl.

3. The method of claim 1 wherein said composition is used in combination with one or more of the following: shampoos, aftershaves, liquid soaps, bar soaps, bath oil bars, shaving creams, dishwashing liquids, detergents, surface cleaners, disposable wipes, conditioners, hair relaxers, hair bleaches, hair detangling lotion, spray foams, shower gels, bubble baths, hair coloring preparations, color conditioners, coloring and non-coloring hair rinses, hair tints, hair wave sets, permanent waves, curling, and hair grooming aids.

4. The method of claim 1 wherein, the polyacrylamides are composed of at least about 50 mole percent acrylamide.

5. The method of claim 3 wherein the polyacrylamides are modified by transamidation with about 0.1 to about 10 mole percent of one or more hydrophobic amines.

6. The method of claim 3 wherein the polyacrylamides are modified by transamidation with about 0.1 to about 50 mole percent of one or more hydrophobic amines.

7. The method of claim 6 wherein the anionic monomers are selected from the group consisting of acrylic acid, 2-acrylamido-2-methylpropanesulfonic acid, and styrene sulfonic acid.

8. The method claim 5 wherein the hydrophobic amines are selected from the group consisting of $C_6$-$C_{22}$ alkyl amities and amino-functionalized silicones.

9. The method of claim 7 wherein the hydrophobic amines are selected from the group consisting of $C_6$-$C_{22}$ alkyl amines and amino-functionalized silicones.

10. The method of claim 9 wherein the polyacrylamide is acrylamide/acrylic acid copolymer.

11. The method of claim 1 wherein said hydrophobically modified polyacrylamides have a weight average molecular weight of about 10,000 to 10,000,000.

12. The method of claim 10 wherein the alkyl amines are selected from the group consisting of octylamine, dodecylamine, hexadecylamine.

13. The method of claim 10 wherein the alkyl amines are selected from the group consisting of amino-functionalized silanes.

14. The method of claim 1 wherein the composition further comprising one or more cosmetically acceptable excipients.

15. The method of claim 14 wherein the one or more cosmetically acceptable excipients are selected from the group consisting of water, saccharides, surface active agents, humectants, petrolatum, mineral oil, fatty alcohols, fatty ester emollients, waxes and silicone-containing waxes, silicone oil, silicone fluid, silicone surfactants, volatile hydrocarbon oils, quaternary nitrogen compounds, amine functionalized silicones, conditioning polymers, rheology modifiers, antioxidants, sunscreen active agents, di-long chain amines from about $C_{10}$ to $C_{22}$, long chain fatty amines from about $C_{10}$ to $C_{22}$, fatty alcohols, ethoxylated fatty alcohols and di-tail phospholipids.

16. The method of claim 14 comprising about 0.01 to about 40 weight percent of hydrophobically modified polyacrylamides, based on actives.

17. The method of claim 1 wherein the hydrophobically modified polyacrylamides further comprise one or more nonionic monomers.

18. The method of claim 1, wherein the composition is applied to the substrate and rinsed from the substrate before or after application of sunscreens, lotions, hand and body creams, latex paints, permanent waves, styling gel, styling glazes, styling creams, styling waxes, styling lotions, mousses, spray gels, pomades, temporary and permanent hair colors, hair lightener's, hair straighteners, hair tonics, hair dressings and oxidative products, spritzes, styling waxes and balms.

* * * * *